US006277882B1

(12) United States Patent
Joshi et al.

(10) Patent No.: US 6,277,882 B1
(45) Date of Patent: Aug. 21, 2001

(54) UTILIZATION OF ALKYL HYDROGEN FUMARATES FOR TREATING PSORIASIS, PSORIATIC ARTHRITIS, NEURODERMATITIS AND REGIONAL ENTERITIS

(75) Inventors: Rajendra K. Joshi, Zürich; Hans-Peter Strebel, Muri, both of (CH)

(73) Assignee: Fumapharm AG, Muri (CH)

(*) Notice: Subject to any disclaimer, the term of this patent is extended or adjusted under 35 U.S.C. 154(b) by 0 days.

(21) Appl. No.: 09/402,103

(22) PCT Filed: Dec. 8, 1998

(86) PCT No.: PCT/EP98/07956

§ 371 Date: Sep. 27, 1999

§ 102(e) Date: Sep. 27, 1999

(87) PCT Pub. No.: WO99/49858

PCT Pub. Date: Oct. 7, 1999

(30) Foreign Application Priority Data

Mar. 31, 1998 (DE) .............................. 198 14 358

(51) Int. Cl.⁷ .............................. A61K 31/225
(52) U.S. Cl. .............................. 514/547
(58) Field of Search .............................. 514/547, 825, 514/863

(56) References Cited

U.S. PATENT DOCUMENTS

| | | | |
|---|---|---|---|
| 4,515,974 | * 5/1985 | Zecher et al. | 549/371 |
| 4,959,389 | 9/1990 | Speiser et al. | 514/494 |
| 5,214,196 | * 5/1993 | Blank | 560/169 |
| 5,242,905 | * 9/1993 | Blank | 514/19 |
| 5,359,128 | * 10/1994 | Blank | 560/169 |
| 5,424,332 | 6/1995 | Speiser et al. | 514/547 |
| 5,548,059 | * 8/1996 | Bayley et al. | 528/194 |
| 5,972,363 | * 10/1999 | Clikeman et al. | 424/408 |

FOREIGN PATENT DOCUMENTS 3834794   4/1990   (DE) .
0312697   4/1989   (EP) .

OTHER PUBLICATIONS

Sebök, Bela et al., "Antiproliferative and Cytotoxic profiles of Antipsoriatic Fumaric Acid Derivatives in Keratinocyte Cultures", European Journal of Pharm., Environ. Toxicol. Pharmacol. Sect., 1994, vol. 270, pp. 79–87.

Nibbering, P.H. et al., "Intracellular Signalling by Binding Sites for the Antipsoratic Agent Monomethylfumarate on Human Granulocytes", British J. Dermatol., 1997, vol. 137, pp. 65–75.

Altmeyer, P. et al., "Systemische Therapie der Psoriasis", T & E Dermatologie Jg., 1997, vol. 27, pp. 380–382, & 384.

Nibbering, Peter H., "Effects of Monomethylfumarate on Human Granulocytes", Journal of Investigative Dermatology, 1993, pp. 37–42.

* cited by examiner

Primary Examiner—William R. A. Jarvis
Assistant Examiner—Vickie Kim
(74) Attorney, Agent, or Firm—Siebarth & Patty, L.L.C.

(57) ABSTRACT

The use of one or several alkyl hydrogen fumarates of the general formula

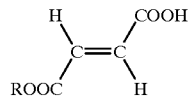

wherein R is a $C_{1-5}$ alkyl, optionally in admixture with dialkyl fumarate of the formula

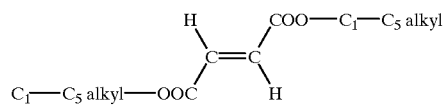

and optionally customary pharmaceutical excipients and carriers for preparing a pharmaceutical composition in the form of micro-tablets or micro-pellets for treating psoriasis, psoriatic arthritis, neurodermatitis and enteritis regionalis Crohn.

20 Claims, No Drawings

UTILIZATION OF ALKYL HYDROGEN FUMARATES FOR TREATING PSORIASIS, PSORIATIC ARTHRITIS, NEURODERMATITIS AND REGIONAL ENTERITIS

The present invention relates to the use of the free acid form of certain fumaric acid monoalkyl esters (alkyl hydrogen fumarates) either alone or in combination with a dialkyl fumarate for preparing a pharmaceutical composition in the form of micro-tablets for treating psoriasis, psoriatic arthritis, neurodermatitis and enteritis regionalis Crohn.

Pharmaceutical preparations which, as a result of biological degradation after administration, lead into the citric acid cycle or belong do that cycle are increasingly gaining significance in generally high dosages, since it is possible to relieve or cure cryptogenetic diseases with their aid.

Thus, fumaric acid inhibits the growth of the Ehrlich ascites tumour in mice, reduces the toxic effects of Mitomycin C and Aflatoxin [cf. K. Kuroda, M. Akao, Biochem. Pharmacol. 29, 2839–2844 (1980)/Gann. 72, 777–782 (1981)/Cancer Res. 36, 1900–1903 (1976)] and has a both anti-psoriatic and antimicrobial effect [C. N. Huhtsnen, J. Food Sci. 48, 1574 (1983)/M.N. Islam, U.S. Pat. No. 4,346, 118/C.A. 97, 161317b (1982)].

When administered by the parenteral, dermal and particularly the oral route, high dosages of the fumaric acid derivatives previously known for this purpose such as dihydroxy fumaric acid, fumaramide and fumaronitrile have such an unacceptable rate of side effects and high toxicity [P. Holland, R. G. White, Brit. J. Dermatol. 85, 259–263 (1971)/M. Hagedorn, K. W. Kalkoff, G. Kiefer, D. Baron, J. Hug, J. Petres, Arch. Derm. Res. 254, 67–73, (1975)] that such a therapy usually had to be disregarded.

EP-A-0 188 749 already describes fumaric acid derivatives (salts) and pharmaceutical compositions containing the same for the treatment of psoriasis.

Pharmaceutical compositions for treating psoriasis which contain a mixture of fumaric acid and other fumaric acid derivatives are known from DE-A-25 30 372. A content of fumaric acid is obligatory.

DE-A-26 21 214 describes drugs for treating psoriasis which contain fumaric acid monoethyl ester and mineral salts thereof as the active ingredient. Moreover, EP-A-0 312 697 describes the use of various fumaric acid monoalkyl ester salts for the therapy of psoriasis, psoriatic arthritis, neurodermatitis and enteritis regionalis Crohn.

The use of fumaric acid monoethyl ester salts (Ca, Zn, Mg) and fumaric acid dimethyl ester for the treatment of psoriasis is known from the publication "Hautarzt"(1987), 279–285.

Since, in a psoriatic epidermis, the activity of phosphoslipase $A_2$ is changed, the fact that this enzyme is stimulated by fumaric acid is one possible explanation of the mechanism of the compositions according to the invention.

Surprisingly, we have now found that the treatment of psoriasis with alkyl hydrogen fumarates even without salt formation can be achieved with a pharmaceutical composition which contains the free acid form of one or several $C_{-1-5}$-alkyl hydrogen fumarates and, optionally, pharmaceutically acceptable excipients and carriers and is presented in the form of micro-tablets or micro-pellets. Optionally, these compositions may also contain one or several dialkyl fumarates.

The compositions in the form of micro-tablets or micro-pellets permit the administration of the free acid instead of its salt without the occurrence of the known side effects, especially the formation of ulcers. This is probably due to the fact that micro-tablets or micro-pellets permit a uniform distribution in the stomach, thus avoiding irritating local concentrations of the monoalkyl hydrogen fumarate in the form of the free acid.

Compositions containing the free acid of the alkyl hydrogen fumarate in an amount of 20 to 300 mg are particularly suitable for oral administration, the total weight of the active ingredients being 100 to 300 mg.

For the systemic start of a therapy or the cessation thereof, respectively, a low dosage containing 100 of 120 mg of active ingredient, e.g. 30.0 mg to 35.0 mg of dimethyl fumarate and 70 to 90 mg of methyl hydrogen fumarate, is advantageous.

190 to 210 mg of active ingredient, e.g. in the form of 120.0 mg of dimethyl fumarate and 90.0 mg of monoethyl fumarate, are an example of a therapeutic dosage after the initial phase.

The compositions according to the invention are administered orally in the form of micro-tablets or encapsulated micro-tablets or micro-pellets, the solid single dosage drug forms dissolving in the stomach within a few minutes and uniformly releasing the active ingredients from the drug form. A lower dosage is required for the start or cessation of systemic treatment and a higher dosage for therapeutic treatment after the initial phase.

The micro-tablets according to the invention are made by methods known in the prior art, such as granulation, screening, extrusion/spheronisation and such like. In addition to the active ingredient, they may contain customary excipients and carriers such as lactose, PVP and such like. The micro-tablets or micro-pellets preferably have a size of 300–2,000 $\mu$m, preferably 500 to 1,500 $\mu$m and even more preferably 1,000 $\mu$m.

To facilitate administration of the single dosage, the micro-tablets or micro-pellets may be encapsulated, for example in gelatinous capsules. Optionally, the micro-tablets or micro-pellets may be provided with a coating which is resistant to gastric acid. Such a coating may be applied with known processes, e.g. by application or spraying in a fluidised bed apparatus or in the form of a film coating.

EXAMPLE

Production of Encapsulated Micro-pellets Containing 50.0 mg of Methyl Hydrogen Fumarate (corresponding to a total of 44.6 mg of fumaric acid)

Taking the necessary precautions (breathing mask, gloves, protective suit), 5,000 kg of methyl hydrogen fumarate are crushed by means of a #400 screen and homogenised. In addition, 21 of a 20% (m/v) polyvinyl pyrrolidone (Kollidon K30) solution in ethanol are prepared. 7.250 kg of Nonpareilles pellets are introduced into a coating pan and sprayed with part of the Kollidon K-30 solution until slightly humid. Then the active ingredient mixture is added in portions until the pellets are dry. This procedure of humidifying/drying is continued until all of the active ingredient mixture has been added. Finally, the pellets are moved around until fully dry. After that, the pellets are filled into hard gelatine capsules (126.5 mg pellets/capsule).

It was found that the preparations according to the invention have an effect similar to that of preparations containing the known fumaric acid derivatives in salt form against various clinical forms of psoriasis, psoriatic arthritis, neurodermatitis and enteritis regionalis Crohn (morbus Crohn), but are free of the side effects known from the administration of the free acid.

Examination of Acute Toxicity

Before the clinical trial, the acute toxicity of methyl hydrogen fumarate was tested by oral administration to rats. The results show a very low toxicity of the fumaric acids used (cf. Table 2).

TABLE 1

Acute toxicity on rats (oral administration)

|  | Sex | Methyl hydrogen fumarate |
|---|---|---|
| $LD_{50}$ | Male | 2,606.8 |
|  | Female | 1,777.8 |
| Lowest lethal | Male | 2,150.0 |
| dose in mg/kg | Female | 1,470.0 |

Pharmaceutical Equivalency

Comparison of the pharmaco-kinetic data of Fumaderm forte (example 4 from European patent 0 312 697 B1) and monomethyl fumarate or monoethyl fumarate, respectively, as calcium salt.

TABLE 2

| | | | Equivalency |
|---|---|---|---|
| Substance administered | Species | Dosage (mg/kg body-wt.) | Methyl hydrogen fumarate level ($C_{max}$)/ ($\mu$g/ml) |
| Fumaderm forte | Rat | 30 | 8,99 |
| Methyl hydrogen fumarate | Rat | 100 | male: 69.9 female: 84,8 |
| Methyl hydrogen fumarate calcium salt | Rat | 100 | male: 51.3 female: 107.0 |

Fumaderm forte: This mixture contains 120 mg of dimethyl fumarate, 87 mg of monoethyl fumarate calcium salt, 5 mg of monoethyl fumarate magnesium salt, 3 mg of monoethyl fumarate zinc salt.

What is claimed is:

1. A method of preparing a pharmaceutical composition for treating psoriasis, psoriatic arthritis, neurodermatitis, or enteritis regionalis Crohn, which method comprises forming micro-tablets or micro-pellets from at least one alkyl hydrogen fumarate of the general formula

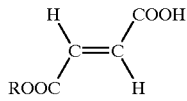

wherein R is a $C_{1-5}$ alkyl, optionally in admixture with dialkyl fumarate of the formula

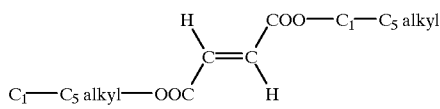

and, optionally, at least one pharmaceutically acceptable excipient or carrier, wherein the said micro-tablets or micro-pellets have a size of about 2,000 $\mu$m or less.

2. The method according to claim 1, wherein methyl hydrogen fumarate is the alkyl hydrogen fumarate used in forming said composition.

3. The method according to claim 2, wherein said methyl hydrogen fumarate is in admixture with dimethyl fumarate.

4. The method according to any of claims 1 to 3, wherein the pharmaceutical composition is adapted for oral administration, and the total weight of the active ingredient (s) per dosage of said composition is 20 to 300 mg.

5. The method according to any of claims 1 to 3, wherein said composition contains 10 to 290 parts by weight of methyl hydrogen fumarate and 290 to 10 parts by weight of dimethyl fumarate per dosage of said composition.

6. The method according to any of claims 1 to 3, wherein the micro-tablets or micro-pellets are adapted for oral administration, and are provided with an enteric coating.

7. The method according to any of claims 1 to 3, wherein the micro-tablets or micro-pellets have a size of 300 to 2,000 $\mu$m.

8. The method according to any of claims 1 to 3, wherein the pharmaceutical composition is adapted for oral administration and the total weight of the active ingredient(s) in said composition per dosage is 20 to 300 mg, and in that said composition contains per dosage 10 to 290 parts by weight of methyl hydrogen fumarate and 290 to 10 parts by weight of dimethyl fumarate.

9. The method according to claim 8, wherein the micro-tablets or micro-pellets are provided with an enteric coating.

10. The method according to claim 8, wherein the micro-tablets or micro-pellets have a size of 300 to 2,000 $\mu$m.

11. A pharmaceutical composition in the form of micro-tablets or micro-pellets and comprising at least one alkyl hydrogen fumarate of the formula

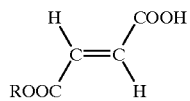

wherein R is a $C_{1-5}$ alkyl, optionally in admixture with dialkyl fumarate of the formula

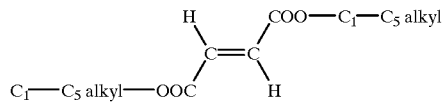

and, optionally, at least one pharmaceutically-acceptable excipient or carrier, wherein the said micro-tablets or micro-pellets have a size of about 2,000 $\mu$m or less.

12. A composition according to claim 11, wherein an active ingredient used in forming in said composition is methyl hydrogen fumarate.

13. A composition according to claim 11, wherein active ingredients used in forming said composition are methyl hydrogen fumarate mixed with dimethyl fumarate.

14. A composition according to any of claims 11 to 13, wherein the pharmaceutical composition is adapted for oral administration, and the total weight of the active ingredient (s) per dosage of said composition is 20 to 300 mg.

15. A composition according to any of claims 11 to 13, wherein said composition contains 10 to 290 parts by weight of methyl hydrogen fumarate and 290 to 10 parts by weight of dimethyl fumarate.

16. A composition according to any of claims 11 to 13, wherein the pharmaceutical composition is adapted for oral administration, and the micro-tablets or micro-pellets are provided with an enteric coating.

17. A composition according to any of claims 11 to 13, wherein the micro-tablets or micro-pellets have a size of 300 to 2,000 $\mu$m.

18. A composition according to any of claims 11 to 13, wherein the pharmaceutical composition is adapted for oral administration, and the total weight of the active ingredients in said composition per dosage is 20 to 300 mg, and in that said composition contains per dosage 10 to 290 parts by weight of methyl hydrogen fumarate and 290 to 10 parts by weight of dimethyl fumarate.

19. A composition according to claim 18, wherein in that the micro-tablets or micro-pellets are provided with an enteric coating.

20. A composition according to claim 18, wherein the micro-tablets or micro-pellets have a size of 300 to 2,000 µm.

* * * * *

UNITED STATES PATENT AND TRADEMARK OFFICE
CERTIFICATE OF CORRECTION

PATENT NO. : 6,277,882 B1 Page 1 of 1
DATED : August 21, 2001
INVENTOR(S) : Rajendra K. Joshi et al.

It is certified that error appears in the above-identified patent and that said Letters Patent is hereby corrected as shown below:

<u>Title page,</u>
Item [74], *Attorney, Agent, or Firm* - reads "Siebarth & Patty, L.L.C." and should read -- Sieberth & Patty, L.L.C. --.

Signed and Sealed this

Twelfth Day of March, 2002

*Attest:*

*Attesting Officer*

JAMES E. ROGAN
*Director of the United States Patent and Trademark Office*